Figure 1:
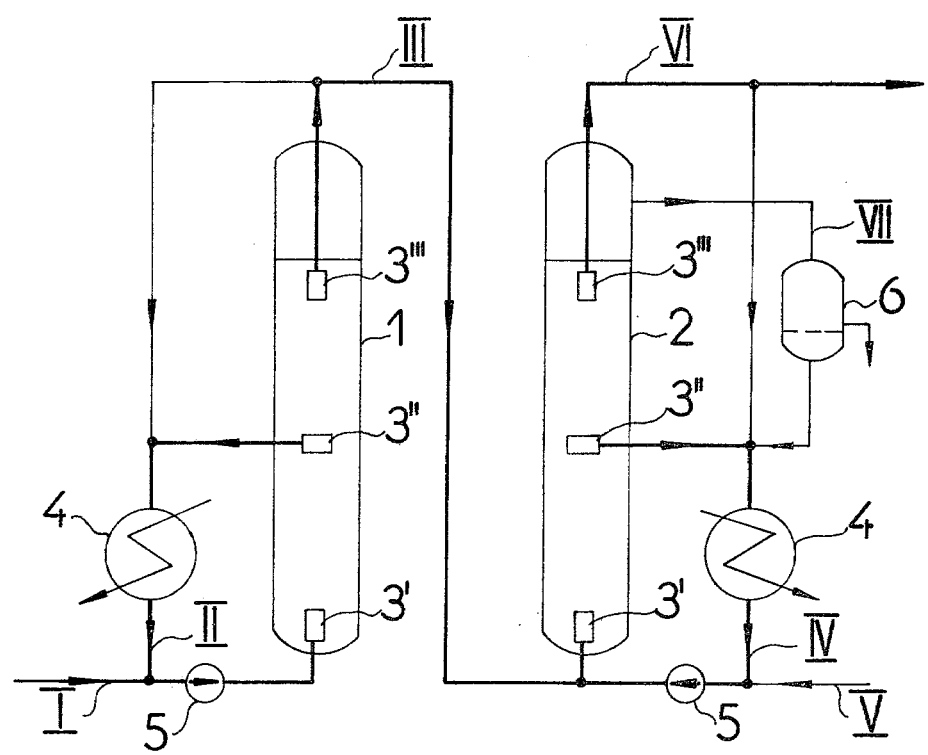

United States Patent [19]

Kiedik et al.

[11] 4,301,305
[45] Nov. 17, 1981

[54] CONTINUOUS PROCESS FOR PREPARATION OF DIAN

[75] Inventors: Maciej Kiedik, Gliwice; Józef Kołt, Zabrze; Jerzy Czyż, Kędzierzyn-koźle; Edward Grzywa, Warsaw; Anna Niezgoda; Kazimierz Terelak, both of Kedzierzyn-Kozle, all of Poland

[73] Assignee: Instytut Ciezkiej Syntezy Organicznej "Blachownia", Kedzierzyn-Kozle, Poland

[21] Appl. No.: 108,403

[22] Filed: Dec. 28, 1979

[30] Foreign Application Priority Data

Dec. 30, 1978 [PL] Poland .................. 212470

[51] Int. Cl.³ .................................. C07C 39/12
[52] U.S. Cl. .................................. 568/727; 568/728
[58] Field of Search .................. 568/727, 728, 788

[56] References Cited

U.S. PATENT DOCUMENTS

| 3,049,568 | 8/1962 | Apel et al. | 568/728 |
| 3,049,569 | 8/1962 | Apel et al. | 568/728 |
| 3,153,001 | 10/1964 | Apel et al. | 568/728 |
| 3,172,916 | 3/1965 | Wagner | 568/728 |
| 4,045,379 | 8/1977 | Kwantes | 568/728 |
| 4,191,843 | 3/1980 | Pieter | 568/728 |

FOREIGN PATENT DOCUMENTS

| 96346 | 5/1978 | Poland | 568/728 |
| 49138 | 12/1967 | Romania | 568/728 |

*Primary Examiner*—Werren B. Lone
*Attorney, Agent, or Firm*—Haseltine and Lake

[57] ABSTRACT

The dian is prepared by the condensation of phenol with acetone in the presence of acid ion-exchange catalyst of the type of sulfonated co-polymer of styrene and divinylbenzene. The three-stage process is conducted in two reactors packed with a stationary catalyst bed. In each of the reactors the bed height is 5–20 m and in addition, in both reactors the beds are divided into bottom and upper zones.

At various stages of the process, a reaction mixture is circulated with a different linear velocity, the first step of the process being conducted at a temperature of 60°–85° C. in the bed of the first reactor, in succession in the bottom and then upper zone of the catalytic bed; the second stage of the process is accomplished in the bottom zone of the second reactor at a temperature of 70°–90° C.; and the third step is carried out in the upper zone of the second reactor at a temperature of 75°–95° C.

The linear velocity of the reaction mixture flow through the bottom zones of the bed is not greater than 10 m/h, and the linear velocity of flow through the upper zones of the reactor bed is not higher than 4 m/h.

The sequence of the reaction mixture flow through the reactors is being changed in cycles, and at interstage intervals the reaction mixture is filtered to separate minus mesh and comminuted particles of the catalyst.

4 Claims, 2 Drawing Figures

CONTINUOUS PROCESS FOR PREPARATION OF DIAN

This invention relates to a method for continuous production of dian by condensation of phenol with acetone in the presence of acid ion-exchange catalyst.

Dian is used as intermediate product for manufacturing epoxy resins, polyacrylates, polysulfones and antipyrenes. A method, generally employed in production of dian, is a condensation of phenol with acetone in the presence of acid catalysts, such as inorganic acids of HCl and $H_2SO_4$ types and Friedel-Crafts catalysts, e.g. $BCl_3$ and $BF_3$. Sometimes, derivatives of hydrogen sulfide are used as a promoter of the reaction.

Partially esterified with mercaptoalcohols, a sulfonated ion-exchange resin of the sulfonated styrene and divinylbenzene co-polymer type is also known to be used as a catalyst in the condensation of phenol with acetone. Such solution is described in U.S. Pat. Nos. 3,049,568 and 3,049,569.

There is known a similar solution proposed by Rumanian Pat. No. 49138, in which, apart from using a catalyst in the form of sulfonated ion-exchange resin partially esterified with mercaptans, a soluble compound of divalent sulfur in an amount of 1–10 wt. % is additionally introduced into a reaction mixture.

The methods described in the aforesaid U.S. Patent Specifications consist in single passing a reaction mixture through a cation exchanger bed using inconsiderable reaction mixture stream flows to assure a contact time with the catalyst in a range of 1 hour. Hence, about 50% conversion in terms of acetone may be obtained, with a dian content in post-reaction mixture not exceeding 13–15 wt. %. Such dian lean post-reaction mixtures produce several problems when separation and purification of the dian are concerned, and react negatively on the economics of the whole process.

The known method of producing dian according to the Polish Pat. No. 96346 is based on condensation of phenol with acetone in the presence of acid ion-exchange catalyst of the type of sulphonated co-polimer of styrene and divinylbenzene with a multiple circulation of the reaction mixture through a catalyst bed, and the process is a three-stage one. During the first stage a mixture composed of phenol and acetone, and containing also dian and by-products resulting from the condensation said mixture having such a composition that molar ratio of phenol to acetone is in the range of 5–30:1, preferably 10–15:1, is circulated until a conversion of the introduced acetone amounts to 20–50%. In the second stage to the reaction mixture circulating through the catalyst bed, acetone is batched in such an amount that its concentration is being maintained in a range of 8 to 1,5 wt. % of the circulating reaction mixture and a total molar ratio of phenol to the total amount of acetone introduced is in the range of 3–10:1. In the third stage the reaction mixture is circulated through the catalyst bed to reduce the content of acetone in said reaction mixture to the amount of 1–5 wt. %. The process can be carried out with batch or continuous method.

The batch process has still some disadvantages which are typical for not continuous kind of processes, i.e. lower installation efficiency resulting from technological stoppages to charge and discharge the reactors, disparities in product quality caused, among other things, by overheating the catalyst bed packed with a stationary reaction mixture during the production breaks, due to lack of possibility for reaction heat removal.

It was also found, that a continuous process for producting, dian, according to the above mentioned patent at its first stage is carried out most preferably at lower temperatures, na the highest selectivity of the condensation process can be obtained under these conditions.

It came out, that in all three stages a reaction rate of the condensation of phenol with acetone, mainly depends on temperature and to a smaller extent on composition of reaction mixture.

The decreasing of temperature in the stage I of the reaction was made possible by using a catalyst bed of greater volume in this stage than in the stage II and III of the process.

Another important factor that must be taken into consideration, when planning a reaction system for production of dian, is the permeability of the cation exchanging bed and its total resistance of flow i.e. those factors which are dependent on bed depth, granular structure of bed and reaction mixture viscosity contingent on temperature and composition.

When the resistance of flow resulting from excessive depth or unfavourable structure of the bed is too high, it cannot be compensated by using a suitably increased pressure difference on either sides of the bed because it is then subjected to compression, thus the resistance of flow increases even move.

The influence of the latter of the factors augmenting the resistance of flow through the cation exchanger bed, i.e. its structure, can be somewhat improved with a suitable treatment of a catalyst by removing the finest grain fraction during the pretreatment of a cation exchanger for work as the catalyst.

In the process for manufacture of dian, the depth of a cation exchanging bed is limited under conditions of a reaction mixture flowing through it, and even in those cases where its granular structure is favourable it cannot exceed 4–5 m.

The volume of bed in the reactors of known types is not greater than 50 m$^3$, as a diameter of the bed should not, in general, be more than 3–4 m for hydraulic and constructional reasons. Thus, a greater number of reactors are involved with a largelet production to be followed by all negative results concerning utilization and realization economics. It must be mentioned, that when lowering the temperature to improve selectivity of the reaction, one cannot exceed some intrinsic viscosity of the reaction mixture or else a phenomenon of partial imperviousness of the bed occurs. This can be avoided by maintenance of a suitable low concentration of by-products, particularly tar substances and dian, in a charge to the reaction system.

It proves useful to maintain high flow velocity is the reaction mixture through the bed by using a suitable flow intensity of the reaction mixture through the cation exchanger.

To sum up, hitherto known solutions regarding a process for preparing dian as well as reaction system designs, do not fulfill all the requirements for optimization of the process. In particular, the process according to these solutions is not feasible to be carried out continuously in reactors with a large volume of catalyst bed, of the order of 100 m$^3$ and above, and moreover, a multi-stage process cannot be performed with indirect proportioning of acetone and differential temperature of the reaction when cation exchanger volumes are greatly differentiated in particular stages and at the same time, with the possibility of reversal of the reaction mixture flow through the reaction system.

According to the invention, a continuous process of condensation of phenol with acetone is conducted in three stages, two reactors and in two stationary catalyst beds. Each bed is 5–20 m high, being divided additionally into two zones, say bottom and top, and a reaction mixture is circulated with a different linear velocity during different stages of the process.

The first stage of the process is accomplished in the bed of the first reactor, in the bottom zone and next in the upper zone of the catalytic bed at a temperature of 60°–85° C.; the second stage is conducted in the bottom zone of the catalytic bed of the second reactor at a temperature of 65° to 90° C., and the third stage is carried out in the upper zone of the bed of the second reactor at a temperature of 70°–95° C.

In both reactors, the linear velocity of reaction mixture flow through the bottom zones of the bed of ion-exchange catalyst is no more than 10 m/h, and that of reaction mixture flowing through the upper zones of catalyst beds in both reactors is not greater than 4 m/h.

The sequence of the reaction mixture flow through the reactors is changed in cycles, as the activity of catalyst decreases. At inverstage intervals, the reaction mixture is being filtered to separate minus mesh and comminuted particles of catalyst. The boundary of the division of the reactor bed into the upper and bottom zones is defined by a system of injection-filtration nozzles which supplies the bed with reaction mixture and withdraws the mixture from it.

The method according to the invention enables to conduct the three-stage process in two simply designed devices in a catalyst bed of sizeable height, which was not feasible up to the present by using the known reactors, and at the same time with an effective heat abstraction by forced circulation of reaction mixture flux through the catalyst bed and external heat exchanger to ensure a selective course of reaction within the optimum range of temperature.

Because of the type of the process and the kinetics of formation of by-products, it is advantageous that the first reaction stage is conducted at a decreased temperature, i.e. from 60° C. to 85° C., whereas in the next stages it is profitable to use elevated temperatures in the range of 65°–90° C. and 70°–95° C., respectively.

It is possible to carry out the first stage of the reaction at the optimally decreased temperature owing to the fact that approximately twice as large amount of catalyst is used during this stage as compared with the subsequent stages.

By using a flow of the reaction mixture through the bed in upward direction, with the linear velocity in the upper zone of the bed not greater than 4 m/h, it is possible to increase considerably the linear velocity of the flow of the reaction mixture in the bottom zone, which is of great importance for removal of reaction heat without simultaneous expansion of the whole bed. At the same time, under these flow conditions, minus mesh and comminuted catalyst particles are being raised to the surface of catalyst by the reaction liquid stream, while the basic grain is left in the stationary bed. A characteristic feature of the cation exchanger, which operates in reaction medium during preparation of dian, is that the cation exchanger grains are slightly but permanently disintegrated to form undersize and comminuted particles which impair hydrodynamic properties of the bed and possibly foul the product.

The possibility of removing the comminuted particles and minus mesh from the catalyst surface by carrying off a portion of the reaction mixture stream, then filtrating at and recycling to the reaction system is a great advantage of the method according to the present invention.

It has also been found, that periodical changes of sequence of the system feeding greatly influences its prolonged yield. It may be assumed that this is connected with an unidirect selective sorption of some components of the reaction mixture, such as high-molecular by-products and water, by the catalyst bed.

The process according to the invention is conducted in a reaction system, illustrated in FIG. 1, composed of two reactors connected in series, the first 1 and the second 2, an external filtering means being connected to a circulation of the first reactor 1 and/or the second reactor 2 to separate minus mesh and comminuted particles of a catalyst from a reaction mixture.

Figure 2:
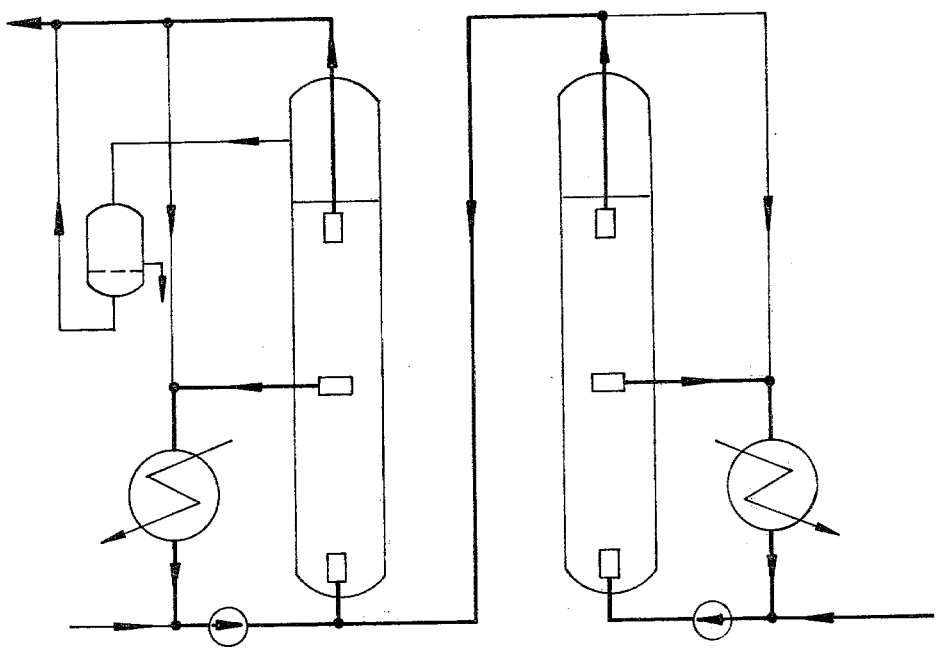

A means for communicating between said reactors makes it possible to change their sequence using the same pumps and heat exchangers. The symmetry of the reaction system assures the maintainance of all its previous parameters after the change of the sequence of the reactors. The reversal of flow is illustrated in FIG. 2.

The process according to the invention is as follows. A charge containing phenol and a portion of acetone introduced into the process, reaches the first reactor 1 from below, flows upward through a catalyst bed by multiple circulations forced with a pump 5, and connected with reaction heat reception in an exchanger 4 then a portion of the stream of the reaction mixture circulating through the catalyst bed in said first reactor flows from the top of the reactor 1 to the reactor 2 from below where the remainder of acetone introduced to the process is being metered, and the reaction mixture flows through the catalyst bed in the second reactor upward in a system of multiple forced circulations consisting in that the portion of the reaction mixture stream which was introduced to the reactor from below is withdrawn from the catalyst bed by means of filtration elements 3 positioned in a middle part of said catalyst bed, and recycled to the reactor from below through said heat exchanger 4 by the pump 5, and the remainder of the stream of the reaction mixture circulates through the upper zone of the bed.

The reaction system, according to the invention may contain 200 m³ and even more of cation exchanger, which was impossible with the previous solutions.

The application of one reaction system, with such a high efficiency, that replaces several smaller systems hitherto designed, enables a reduction of execution and operating costs calculated per production unit.

Service life of the catalytic charge is prolonged many times thanks to removal of the minus mesh and comminuted particles of catalyst as they are being formed. The system can be fully automated.

EXAMPLE

To a reaction system, illustrated in FIG. 1, composed of two reactors with 2400 mm in diameter and 10 000 mm high, and having a cation exchanging bed Wofatit KPS 7500 mm in height, a charge mixture which makes a stream I, comprising 74,5% of phenol, 3,5% of acetone, 11% of dian, 10,5% of by-products and 0,5% of water was introduced at a temperature of 75° C. and at a rate of 12 m³/h. The stream I, together with a circulating stream II, is fed to a reactor I from below by a pump 5 through a system of multi-slot filtration nozzles 3.

The reaction mixtures flows through the catalyst bed upward and is partially withdrawn from the reactor 1 through a system of multi-slot filtration nozzles 3 disposed at the height of 4000 mm from the bottom of the reactor, and is recycled via an external heat exchanger 4 to the bottom section of the reactor 1.

The circulating stream II, with the rate of 20 m³/h, is combined with the feedstock I to form a stream with the rate of 32 m³/h, which flows through the bottom zone of the first reactor with a linear velocity of 7,1 m/h. The remainder of the reaction mixture is possed through the upper zone of the catalyst bed with a linear velocity of 3,3 m/h and a system of multi-slot filtration nozzles 3''' disposed at 2500 mm from the upper bottom of the reactor close under the surface of said catalyst bed, and the main portion is directed to a reactor 2 from below as stream III at the rate of 12 m³/h, the rest of the mixture, with the rate of 3 m³/h, is added to the cycle of reactor 1—to said circulating stream II. In the reactor 1, the temperature of the catalyst bed was in the range of 75° C. to 77° C.

A circulation stream IV and the remainder of acetone introduced into the process as stream V at a rate of 0,5 m³/h are also directed through the filtration nozzles 3' to the bottom zone of the reactor 2.

When the reaction mixture had crossed the bottom zone of the catalyst bed, its portion is withdrawn by the filtration nozzles 3'' disposed at a distance of 4000 m from the bottom of the reactor, and after joining stream VII that flows through a filtration means 6 makes the circulation stream IV with a rate of 16 m³/h recycled to the bottom zone of the reactor 2 through heat exchanger 4 by means of pump 5. The linear velocity of the reaction mixture flow in the bottom zone of the second reactor is 6,3 m/h. The remainder of the reaction mixture flowing through the upper zone of the reactor 2 with a linear velocity of 3,3 m/h is mainly removed by the system of filtration nozzles 3''' disposed at a distance of 2500 mm from the upper bottom of the reactor close underneath the catalyst bed surface and forms a stream VI of a post-reaction mixture at the rate of 12,5 m³/h directed further to be processed.

In the second reactor, the temperature of the bottom and upper zones of the bed is of 78°–80° C. and 80°–82° C., respectively. Comminuted particles and undersize of the catalyst were discharged from the system by the filtration means 6, into which the stream VII of the post-reaction mixture was introduced at a rate of 2 m³/h, said stream after being cleaned was directed within the circulating stream IV back to the bottom zone of the reactor 2 from below.

What we claim is:

1. A method of preparing dian by condensation of phenol with acetone in the presence of acid ion-exchange catalyst of sulfonated copolymer of styrene and divinylbenzene, with multiple circulation of the reaction mixture through a catalyst bed, wherein said process is conducted in three stages, characterized in that said three stages of the process are performed in two reactors in two stationary catalyst beds, each of the beds having a height of 5–20 m, each of said beds being divided into an upper and bottom zone; wherein said reaction mixture is circulated in particular stages of the process with a different linear velocity, said first stage of the process being conducted in the bed of the first reactor in turn in said bottom and then upper zone of the catalytic bed at a temperature of 80°–85° C., said second stage being carried out in the bottom zone of the catalytic bed of the second reactor at a temperature of 65° C. to 90° C., and the third stage of the process being conducted in the upper zone of the second reactor at a temperature of 70° to 95° C., wherein said linear velocity of flow of the reaction mixture through the bottom zones of the catalytic bed in both of the reactors is not greater than 10 m/h, and the linear velocity of flow of the reaction mixture through the upper zones of the catalyst bed in both of the reactors is not greater than 4 m/h.

2. The method of claim 1 wherein the sequence of flow of said reaction mixture through the catalyst beds in both of the reactors is changed in cycles.

3. The method of claims 1 and 2 wherein at least a portion of said reaction mixture is passed by filter to remove undersize and comminuted particles of the catalyst.

4. The method of claim 1 wherein a boundary of the bed divided into the upper and bottom zones in the reactors is defined by a system of injection-filtration nozzles said nozzles supplying the catalyst bed with the reaction mixture or withdrawing said mixture from the bed.

* * * * *